United States Patent [19]
Edwards et al.

[11] Patent Number: 4,931,205
[45] Date of Patent: Jun. 5, 1990

[54] TERTIARY THIOL ETHOXYLATE COMPOSITIONS

[75] Inventors: Charles L. Edwards; Herbert E. Fried; Werner Lilienthal, all of Houston, Tex.

[73] Assignee: Shell Oil Company, Houston, Tex.

[21] Appl. No.: 230,809

[22] Filed: Aug. 9, 1988

[51] Int. Cl.$^5$ ............................................. C07C 148/00
[52] U.S. Cl. ............................. 252/174.21; 252/351; 568/45
[58] Field of Search ............ 252/351, 174.21, DIG. 1; 568/45

[56] References Cited

U.S. PATENT DOCUMENTS

| | | | |
|---|---|---|---|
| 2,565,986 | 8/1951 | Olin | 568/45 |
| 2,820,060 | 1/1958 | Folkins et al. | 260/609 |
| 2,820,061 | 1/1958 | Folkins et al. | 260/609 |
| 2,864,866 | 12/1958 | Louthan | 260/607 |
| 2,905,720 | 9/1959 | de Benneville | 568/45 |
| 3,258,495 | 6/1966 | Le Fave et al. | 260/609 |
| 3,682,849 | 8/1971 | Smith et al. | 260/615 B |
| 4,575,569 | 3/1986 | Edwards | 568/45 |
| 4,665,236 | 5/1987 | Edwards | 568/618 |
| 4,689,435 | 8/1987 | Edwards | 568/618 |

*Primary Examiner*—John F. Niebling
*Assistant Examiner*—Isabelle Rodriguez
*Attorney, Agent, or Firm*—Richard F. Lemuth

[57] ABSTRACT

Certain mixtures of the ethylene oxide adducts of higher carbon number tertiary thiols, having a reduced content of free thiols and lower (i.e., 1 to 3 mol) ethylene oxide adducts, exhibit improved detergency performance, particularly in high temperature laundry applications.

18 Claims, No Drawings

TERTIARY THIOL ETHOXYLATE COMPOSITIONS

BACKGROUND OF THE INVENTION

This invention relates to a particular class of tertiary thiol ethoxylates and to a process for their preparation. More particularly, the invention relates to ethylene oxide adducts of higher carbon number (e.g., $C_9$ to $C_{16}$) tertiary thiols which exhibit improved detergency performance. The thiol ethoxylates of interest are characterized by a substantially reduced content of free thiols and lower ethylene oxide adducts, relative to their conventional counterparts.

A variety of products useful, for instance, as nonionic surfactants, solvents, and chemical intermediates, have been conventionally prepared by the addition of ethylene oxide to alkane thiols. An illustration of the preparation of a thiol ethoxylate (represented by formula III below) by addition of a number (n) of ethylene oxide molecules (formula II) to a single alkane thiol molecule (formula I) is presented by the equation

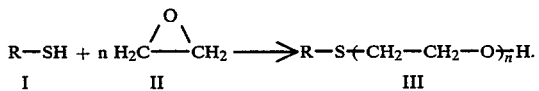

wherein R is alkyl and n, representing the product's ethylene oxide adduct number, is an integer equal to or greater than one.

Of particular interest to the present invention are tertiary thiol ethoxylates in which the alkyl R group of the thiol ethoxylate molecule has a carbon number in the range from about 9 to about 16. These materials are known to have utility as components of detergent formulations and as spermicidal agents.

Any given ethylene oxide addition reaction is known to produce a mixture of various ethoxylate molecules having different numbers of ethylene oxide adducts (oxyethylene adducts), i.e., having different values for the adduct number n in formula III above. Tertiary thiol ethoxylate products prepared in this manner are, as a rule, sold and used in the form of such mixtures, having a statistical distribution of adduct numbers which is characteristic of the reaction, taking into account the relative amounts of reactants used. Such mixtures also characteristically contain a certain amount of unreacted (or "free") thiol. The conventional designation of thiol ethoxylates, in terms of ethylene oxide adduct number, represents a calculated average value for the number of ethylene oxide adducts per thiol ethoxylate molecule in the mixture.

The present invention most particularly relates to tertiary thiol ethoxylate mixtures having unique and beneficial ethylene oxide adduct distributions and low concentrations of free thiol.

SUMMARY OF THE INVENTION

It has now been found that certain thiol ethoxylate compositions having specified low levels of free thiol and the lower ethylene oxide adducts have substantially improved performance as laundry detergents in high temperature applications. The compositions of the invention further exhibit improved physical properties which facilitate their formulation into multi-component detergent product formulations.

Accordingly, in one aspect, the present invention is a composition comprising a mixture of ethoxylates of $C_9$ to $C_{16}$ tertiary thiols, which mixture contains limited amounts of free thiol and lower ethylene oxide adducts, specifically a mixture having (i) an average ethylene oxide adduct number which is in the range from about 5 to 12 inclusive, (ii) a concentration of free thiol which is less than about 0.08 percent by weight, (iii) a concentration of thiol ethoxylates having an ethylene oxide adduct number of one which is less than about 0.1 percent by weight, (iv) a concentration of thiol ethoxylates having an adduct number of two which is less than about 0.1 percent by weight, and (v) a concentration of thiol ethoxylates having an ethylene oxide adduct number of three which is less than about 1.6 percent by weight.

In another aspect, this invention is a process of the preparation of such tertiary thiol ethoxylates. It has been found that products according to the invention are prepared in a process which comprises the steps of (a) contacting and reacting, under thiol ethoxylation conditions and in the presence of a thiol ethoxylation catalyst, (i) one or more tertiary alkane thiols of the formula

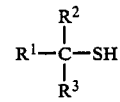

wherein $R^1$, $R^2$, and $R^3$ each individually represents an alkyl group having a carbon number in the range from about 1 to 10 and the sum of the carbon numbers of $R^1$, $R^2$, and $R^3$ is in the range from about 8 to 15, with (ii) sufficient ethylene oxide to produce a mixture of tertiary thiol ethoxylates of the formula

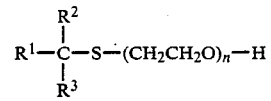

wherein n represents the ethylene oxide adduct number of the thiol ethoxylate molecule and n has an average value for the mixture which is in the range from about 4.5 to 11.5, said mixture also containing about 0.1 percent or more by weight of free thiol, and (b) heating the resulting tertiary thiol and tertiary thiol ethoxylate mixture to evaporate sufficient free thiol and lower ethylene oxide adducts to reduce the mixture's concentration of (i) free thiol to less than about 0.08 percent by weight, (ii) thiol ethoxylates having an ethylene oxide adduct number of one to less than about 0.1 percent by weight, (iii) thiol ethoxylates having an adduct number of two to less than 0.1 percent by weight, and (iv) thiol ethoxylates having an ethylene oxide adduct number of three to less than about 1.6 percent by weight.

The improved performance of the compositions of the invention is considered to have substantial value in commercial practice. Ethoxylates of $C_{11}$ to $C_{16}$ tertiary thiols are known to find a major end use in industrial laundry services, which are characterized by high temperature wash solutions, e.g., about 130° to 180° F. The compositions of the invention very fortuitously and unexpectedly exhibit improved detergency performance at the high temperatures of conventional industrial laundry services, even though their low temperature laundry detergency is not distinguishable from that of conventional tertiary thiol ethoxylates. Moreover, use of the compositions of the invention has been shown to reduce the number of fresh water rinses required in laundry applications.

The improved formulability properties of the compositions of the invention also favor their use in industrial services, where it is common to prepare, handle and store detergents in highly concentrated form.

DETAILED DESCRIPTION OF THE INVENTION

Tertiary thiol ethoxylate compositions of this invention differ from prior art counterparts with respect to the relative content in the composition of free thiol and of the lower adduct number thiol ethoxylates.

The compositions are necessarily characterized in the first instance as comprising mixtures of tertiary thiol ethoxylate molecules of the formula $$R-S-(CH_2-CH_2-O)_n H,$$

wherein R is a tertiary alkyl group having a number of carbon atoms in the range from 9 to 16 and n is an integer representing the number of ethylene oxide adducts. The average value of n for the $C_9$ to $C_{16}$ tertiary thiol ethoxylates in the composition is necessarily in the range from about 5 to 12, more preferably in the range from about 6 to 10, and most preferably in the range from about 6.5 to 7.5. The carbon number range of 9 to 16 is important from the standpoint of the performance of the tertiary thiol ethoxylates as laundry detergents.

The composition of the invention is a mixture of thiol ethoxylates, substantially free of unethoxylated thiols. The composition suitably contains less than about 0.08 percent by weight (% w) of $C_9$ to $C_{16}$ thiols, although preference exists for a composition containing lesser amounts of the tertiary thiols, particularly less than about 0.06% w, most particularly less than about 0.03% w. Prior art ethoxylates of $C_9$ to $C_{16}$ tertiary thiols, having an average ethylene oxide adduct number in the range from 5 to 12, characteristically contain about 0.1% w or more of free thiols, particularly between about 0.15% and 0.5% w, representing residual thiols which do not react with ethylene oxide during ethoxylate preparation. (In each case, these specifications refer to the percentage by weight of free $C_9$ to $C_{16}$ tertiary thiols relative to the total weight in the mixture of ethoxylates of $C_9$ to $C_{16}$ tertiary thiols.

The composition of the invention is further restricted with respect to its content of the lower adduct tertiary thiol ethoxylates, i.e., those having ethylene oxide adduct numbers in the range from 1 to 3, inclusive. For purposes of the desired properties and performance, it has been found necessary to limit the suitable content of the $C_{11}$ to $C_{16}$ tertiary thiol ethoxylate molecules having an adduct number of one to a quantity less than about 0.1% w, preferably to a quantity less than about 0.05% w and most preferably to a quantity less than about 0.01% w; tertiary thiol ethoxylate molecules having an adduct number of two are present in a quantity less than about 0.1% w, preferably less than about 0.06% w, and most preferably less than about 0.03% w; and tertiary thiol ethoxylate molecules having an adduct number of three are present in a quantity less than about 1.6% w, preferably less than about 1.0% w, and most preferably less than about 0.6% w. In each case, these specifications upon the quantity of each lower adduct thiol ethoxylates refer to the percentage by weight of the particular adduct number ethoxylate, relative to the total weight in the mixture of all ethoxylates of $C_9$ to $C_{16}$ tertiary thiols. The restrictions (for a composition containing less than about 0.1% w of ethoxylates having an adduct number of one, less than about 0.1% w of ethoxylates having an adduct number of two, and less than about 1.6% w of ethoxylates having an adduct number of three) represent the level ethylene oxide adducts 1, 2 and 3 in the composition of the invention and is only about one-half the corresponding level in conventional $C_9$ to $C_{16}$ tertiary thiol ethoxylates.

In order to obtain the benefits of this invention, it has been found to be particularly important to restrict the composition's content of free thiols and of $C_9$ to $C_{16}$ tertiary thiol ethoxylates having adduct numbers of 2 or less (i.e., ethoxylates having an adduct number of either 1 or 2). It is these components of conventional thiol ethoxylate products which are believed to have the greatest adverse influence upon their detergent performance and physical properties and formulability. In this respect, it is preferable that the composition be essentially free of such components, in particular that it contain a total of less than about 0.2 percent by weight, and more preferably a total of less than about 0.1 percent by weight, of free thiol and $C_9$ to $C_{16}$ thiol ethoxylates having an ethylene oxide adduct number equal to or less than 2.

Tertiary thiol ethoxylate compositions according to the invention may suitably be derived from conventional thiol ethoxylate compositions. In conventional practice, tertiary thiols in the $C_9$ to $C_{16}$ range (most commonly thiols derived by oligomerization of propylene, butylene, or mixtures thereof) are contacted and reacted with sufficient ethylene oxide in the presence of basic catalysts (particularly one or more of the alkali and alkaline earth metals and their oxides and hydroxides) to yield ethoxylates having the average adduct numbers desired for the particular products. Thiol ethoxylation processes are well known in the art—suitable and preferred process procedures and conditions are described in U.S. Pat. No. 4,575,569, the relevant disclosures of which are incorporated herein by this reference.

For the preparation of compositions according to this invention, conventional thiol ethoxylate products may be subjected to evaporation (including distillation) to reduce their contents of the more volatile thiols and the lower adduct number thiol ethoxylates. Preferably, this evaporation step is carried out under reduced (subatmospheric) pressure to facilitate the vaporization of these lighter (lower boiling) components without raising temperature to a level which might result in product degradation. Evaporation pressures of less than 2 mm Hg are preferred, while pressures of less than about 1 mm Hg are considered more preferred. Evaporation temperatures will depend upon the carbon number of the alkyl group (R in the above formula) and upon the pressure. Typical evaporation temperatures are in the range from about 130° to about 210° C. for evaporation under preferred pressure conditions.

Thin film evaporation techniques have proved very useful in preparing compositions according to the invention from conventional tertiary thiol ethoxylate mixtures.

When evaporation procedures are applied to such conventionally produced thiol ethoxylate mixtures to bring their content of thiols and lower adduct number ethoxylates within the specifications recited for this invention, it is preferable (although not critical) that the mixture be one which has been derived from thiols which are predominantly within a carbon number range of at most 3, particularly a carbon number range of at most 2. For instance, evaporation is preferably applied to a mixture wherein the alkyl R groups are either predominantly of a single carbon number in the $C_9$ to $C_{16}$ range or predominantly of two contiguous carbon numbers within that range (e.g., $C_{11}$ and $C_{12}$, $C_{12}$ and $C_{13}$, $C_{13}$ and $C_{14}$, etc.) or predominantly of three contiguous carbon numbers within that range (e.g., $C_{12}$, $C_{13}$, and $C_{14}$, etc.). Most preferably, the mixture subjected to evaporation consists essentially of thiol ethoxylates wherein the R groups are within a contiguous two carbon number range. In this respect, it is particularly preferred that at least 90%, most preferably at least 95% of the thiol ethoxylates in the mixture have carbon numbers within the a contiguous carbon number range. This specification is placed upon R group carbon number to facilitate the evaporation of sufficient lower adduct number ethoxylates, without undue evaporation of higher adduct number ethoxylates. There is a substantial overlap between the boiling points and vapor pressures of the desirable and undesirable components of the mixture as the carbon numbers of the alkyl R groups of the molecules are spread over a greater carbon number range. As a result, the greater the R group carbon number range, the more difficult is the efficient separation by evaporation of only the lighter (lower adduct number) ethoxylates. If the preparation of thiol ethoxylate products having a broader range of alkyl R group carbon numbers is desired, these can be blended from two or more compositions according to the invention which have each been separately prepared via an evaporation step from a mixture of thiol ethoxylates having alkyl R groups within a two contiguous carbon number range.

In the typical case, vapor phase removal of about 4% or more of the conventional thiol ethoxylation mixture is sufficient to bring the content of its residual thiol and lower adduct number ethoxylates within the specification of the invention. Preferably, compositions according to the invention, having an average adduct number of between about 5 and 12, are prepared by evaporation and vapor phase removal of at least about 5% w (particularly between about 5% w and 12% w), more preferably at least about 6% w particularly between about 6% and 10%), of the lower boiling components from a conventionally prepared tertiary thiol ethoxylate mixture. The composition of the resulting composition can be measured (and the evaporation step controlled) using conventional analytical techniques such as gas-liquid chromatography.

It should be understood that removal of lower adduct number ethoxylate components from a conventional tertiary thiol ethoxylate mixture results in a composition which has an increased average adduct number. For instance, if the average adduct number of the conventional tertiary thiol ethoxylate mixture, prior to evaporation, is about 7, the average adduct number of the composition remaining after evaporation of 6% w of the mixture will typically be approximately 7.2 to 7.3.

The present invention specifically encompasses a process wherein thiol ethoxylate compositions according to the invention are prepared by ethoxylating tertiary thiol and heating the resulting mixture of tertiary thiol and tertiary thiol ethoxylates to evaporate sufficient thiol and lower adduct number ethoxylates to bring their contents within the indicated limits.

In the alternative, tertiary thiol ethoxylate compositions according to the invention can be separated from conventional products of thiol ethoxylation reactions by solvent extraction techniques. The lower adduct number ethoxylates are less polar in character and will partition into the nonpolar solvent phase of a two phase extraction medium, while the more polar higher adduct number ethoxylates will partition into the polar phase of such a medium. Solvent extraction of a conventional thiol ethoxylate mixture to produce a composition coming within the specifications for the invention can be accomplished, for instance, by extraction of the mixture in a hydrocarbon (e.g., hexane) and water medium, with the desired product being then recovered in the polar aqueous extraction phase.

The thiol and the lower adduct number ethoxylates separated from a conventional tertiary thiol ethoxylate by evaporation or other means are desirably recovered and recycled for further ethoxylation.

Still other methods for the preparation of compositions according to the invention will be apparent to those of skill in the art.

The invention is further described with reference to the following examples and comparative examples, which are intended to illustrate certain preferred aspects of the invention without limiting its broader scope.

EXAMPLE 1

Preparation of Compositions of the Invention

This example illustrates one preferred method for preparing tertiary thiol ethoxylate compositions of the invention.

A one mol ethylene oxide adduct of a tertiary thiol was first prepared for use as a "seed ethoxylate" promoter in a subsequent thiol ethoxylation reaction. For preparation of this seed, 140 grams of a $C_{12}$ tertiary thiol (a commercial product of the Pennwalt Corporation) and about 0.2 grams of 85% w potassium hydroxide (ethoxylation catalyst) were charged to a 300 ml glass flask. Water was removed by heating the mixture to 130° C. with nitrogen sparge for two hours. The thiol and potassium hydroxide solution was then transferred to a 300 ml autoclave. For ethoxylation of the thiol, a 40%/60% mixture of ethylene oxide and nitrogen was introduced into the autoclave to a total pressure of 60 psig. As the ethoxylation reaction proceeded, 30 grams of additional ethylene oxide was added on demand to maintain pressure. A seed ethoxylate mixture, analyzed to have an average adduct number of 0.99, was obtained after 60 minutes reaction at 60° C.

A tertiary thiol ethoxylates was then prepared from $C_{12}$ tertiary thiol, using the seed ethoxylate as a reaction promoter. A mixture of 1000 grams of $C_{12}$ tertiary thiol with 40 grams of the seed ethoxylate and 6.4 grams of 85% w potassium hydroxide was charged to a 2 liter flask and nitrogen sparged for 1.5 hours at 130° C. The reaction mixture was transferred to a one gallon reactor. A 40%/60% mixture of ethylene oxide and nitrogen was introduced into the autoclave to a total pressure of 60 psig at an initial temperature of 60° C. As ethylene oxide was consumed in the reaction, additional ethylene oxide was added to maintain this pressure.

After 224 grams of ethylene oxide had been added, temperature was increased to 120° C. A total of 1687 grams of ethylene oxide was added over an 8 hour period. Ethylene oxide addition was then discontinued, and the reaction mixture was maintained at 120° C. for an additional 30 minutes to complete the reaction of the ethylene oxide in the reactor. The reaction mixture was then cooled and neutralized with acetic acid. Analysis indicated that the product had an average ethylene oxide adduct number of 7.08, with an adduct number distribution as follows:

| Adduct Number | % w |
| --- | --- |
| 0 (free thiol) | 0.09 |
| 1 | 0.21 |
| 2 | 0.53 |
| 3 | 2.25 |
| 4 | 6.18 |
| 5 | 11.29 |
| 6 | 16.10 |
| 7 | 15.79 |
| 8 | 14.36 |
| 9 | 11.37 |
| 10 | 8.31 |
| 11 | 5.69 |
| 12 | 3.56 |
| 13 | 2.11 |
| 14 | 1.13 |
| 15 | 0.57 |
| 16+ | 0.47 |

Portions of this thiol ethoxylate mixture were then subjected to wiped film evaporation in a glass, laboratory size apparatus, operated under a vacuum of 1.0 to 1.3 mm Hg at a temperature of 130° to 210° C. A series of evaporation runs were made to recover samples, designated "a" through "g", of the liquid ethoxylate mixture, after evaporation of different fractions of the material overhead. The following table indicates for each such sample the total "percent evaporated" overhead before the sample was taken and the distribution in the sample of free thiol and ethoxylates having adduct numbers of 0 (representing free thiol) and 1 through 3.

| Sample | Percent Evaporated | % w Ethoxylate of Adduct Number | | | | Average Adduct Number |
| --- | --- | --- | --- | --- | --- | --- |
| | | 0 | 1 | 2 | 3 | |
| a | 0 | 0.09 | 0.21 | 0.53 | 2.25 | 7.08 |
| b | 1.67 | 0.03 | 0.18 | 0.42 | 1.83 | 7.15 |
| c | 2.49 | 0.02 | 0.10 | 0.21 | 1.62 | 7.18 |
| d | 3.09 | 0.02 | 0.10 | 0.22 | 1.31 | 7.21 |
| e | 6.69 | 0.01 | 0.00 | 0.03 | 0.46 | 7.44 |
| f | 7.66 | 0.01 | 0.00 | 0.02 | 0.40 | 7.45 |
| g | 11.38 | 0.02 | 0.00 | 0.00 | 0.14 | 7.56 |

Only samples e, f, and g come within the scope of this invention. Samples a, b, c, and d were prepared for purposes of the comparative tests presented in Examples 2-4.

EXAMPLE 2

Physical properties and formulability

This example illustrates the improved physical properties and formulability of tertiary thiol ethoxylates according to this invention, particularly in terms of increased cloud point temperatures and also in terms of reduced turbidity at room temperature.

Aqueous mixtures of these several samples prepared according to Example 1 were tested for turbidity and cloud point. Cloud point temperatures were determined for aqueous mixtures containing 1% by weight of an ethoxylate sample in water. The reported cloud point is that temperature at which each such mixture turned cloudy upon heating. Turbidity measurements were made for 1.5% w aqueous mixtures of the several samples at 23° C. Turbidity results are reported as percent transmittance of light, measured with a dipping probe colorimeter. Duplicate runs were made for each turbidity determination.

| Sample | Cloud Point Temperature (°C.) | Turbidity (% Transmittance) | | |
| --- | --- | --- | --- | --- |
| | | Run 1 | Run 2 | Average |
| a | 15.4 | 7.8 | 7.6 | 7.7 |
| b | 16.7 | 8.1 | 7.9 | 8.0 |
| c | 17.8 | 8.2 | 8.3 | 8.3 |
| d | 18.7 | 8.5 | 8.3 | 8.4 |
| e | 23.6 | 73.7 | 78.6 | 76.2 |
| f | 24.5 | 82.2 | 84.3 | 83.3 |
| g | 28.8 | 88.5 | 89.8 | 89.2 |

Both cloud point and turbidity properties are substantially improved in compositions according to the invention. Such improvements facilitate the preparation of clear, one-phase, homogeneous formulations of the tertiary thiol ethoxylates.

EXAMPLE 3

Laundry detergency

The same seven tertiary ethoxylate samples prepared as described in Example 1 above were compared for their performance in laundry detergent service.

For these comparative tests, soiled swatches of permanent press polyester/cotton (65%/35%) fabric were washed under a standard laboratory "terg-o-tometer" laundry test method. Each swatch was soiled with 100 microliters of dirty motor oil. Laundry performance was determined using by comparing light reflectance measurements of made of soiled swatches (each containing 100 microliters of dirty motor oil, before and after laundry, with the reflectance of unsoiled control swatches.

Each terg-o-tometer (a 2,000 ml beaker fitted with a shaft-driven stirrer) was charged with 500 ml of deionized water at either 150° or 170° C. The tertiary thiol ethoxylate being tested was added in an amount to give a concentration of 0.15 grams per liter, and TEA (triethanolamine, 99%) was added as buffer in an concentration of 0.15 grams per liter. 1.5 grams of 50,000 ppm laboratory prepared hard water was also added to simulate 150 ppm water hardness calculated as calcium carbonate.

Each soiled swatch was introduced into a well mixed terg-o-tometer and washed at 100 rpm stirring for 10 minutes. After the wash, the swatch was removed from the wash beaker, gently rinsed in a beaker containing 500 ml deionized water, and then dried.

Performance of the each laundry test was based on measurements of the reflectance (total color difference) of the swatch before and after laundering. Reflectance was determined using a Hunter Labscan II Colorimeter. Soil removal (in percent) was determined by the following formula:

$$\text{soil removal} = 100 \times (R_s - R_w)/(R_s - R_c),$$

where $R_s$ is the measured reflectance value for the soiled swatch, before washing, $R_w$ is the reflectance value for the soiled swatch after washing, and $R_c$ is the reflectance value for the unsoiled control swatch.

As illustrated by the following table, the laundry tests carried out at 150° C. showed a substantial advantage for the compositions of the invention. A significant, although lesser, trend of performance improvement was also found in tests run at 170° C. Results presented in this table were determined on the basis of "DE" total color difference measurements, and represent the average of four experiments.

| Sample | % w Ethoxylate of Adduct Number | | | | % Soil Removal | |
|---|---|---|---|---|---|---|
| | 0 | 1 | 2 | 3 | 150° F. Test | 170° F. Test |
| a | 0.09 | 0.21 | 0.53 | 2.25 | 18 | 16 |
| b | 0.03 | 0.18 | 0.42 | 1.83 | 21 | 17 |
| c | 0.02 | 0.10 | 0.21 | 1.62 | 23 | 21 |
| d | 0.02 | 0.10 | 0.22 | 1.31 | 34 | 19 |
| e | 0.01 | 0.00 | 0.03 | 0.46 | 33 | 18 |
| f | 0.01 | 0.00 | 0.02 | 0.40 | 32 | 21 |
| g | 0.02 | 0.00 | 0.00 | 0.14 | 38 | 24 |

The advantages identified for the compositions of the invention under high temperature wash conditions are considered particularly surprising in view of results of tests run at temperatures of 70° F. For comparison, the laundry test procedures were run using 70° F. wash solution. (As expressed hereinabove, thiol ethoxylates find use in industrial laundry detergent services which are typically run at high temperatures.) The soil in these 70° F. was a mixture of polar particulate soils. The results of the 70° F. tests were as follows, with percent soil removal determined on the basis of "Delta Y" lightness measurements. Two runs of the test were made under the same conditions; each data point for each run represents the average of duplicate runs.

| Sample | Percent Soil Removal at 70° F. | |
|---|---|---|
| | First Run | Repeat Run |
| a | 31 | 38 |
| b | 33 | 38 |
| c | 28 | 35 |
| d | 30 | 35 |
| e | 32 | 35 |
| f | 31 | 33 |
| g | 34 | 34 |

EXAMPLE 4

Laundry rinsing

This example demonstrates that the compositions of the invention can be applied to reduce the number of fresh water rinses in laundry detergent service. It has been found that when the compositions of the invention are applied under industrial laundry conditions, fewer fresh water rinses are necessary to obtain the desired level of cleanliness, relative to conventional tertiary thiol ethoxylates.

Laundry detergency experiments were carried out under the standard terg-o-tometer laboratory test procedures described in Example 3 above. However, the fabric swatches were not immediately rinsed after washing. Each washed swatch was dried after washing, and a reflectance measurement was made of the dried swatch. The swatch was then rinsed and again dried. The rinsing and drying cycle was then repeated a second time. Soil removal was determined (by the "DE" method) after each drying. Soil removal results are presented in the following table, as a function of the thiol ethoxylate sample used and the number of rinses.

| Sample | Soil Removal after Rinsing | | |
|---|---|---|---|
| | No Rinse | One Rinse | Two Rinses |
| a | 14 | 26 | 29 |
| b | 15 | 26 | 29 |
| c | 16 | 29 | 31 |
| d | 17 | 28 | 31 |
| e | 18 | 29 | 31 |
| f | 17 | 27 | 30 |
| g | 19 | 30 | 31 |

These tests suggest that with a large number of rinses, the performance of all of the thiol ethoxylate samples approaches the same level. However, the number of rinses required to reach that level is reduced when using compositions of this invention, in comparison to prior art tertiary thiol ethoxylates. The benefits of minimizing the number of laundry rinses can be realized in reduced water requirements, reduced fuel requirements for water heating, and reduced requirements for effluent water treating.

EXAMPLE 5

Hard surface cleaning tests

The several tertiary thiol ethoxylate samples prepared according to Example 1 were subjected to comparative tests of their hard surface cleaning performance, using the standard hard-surface cleaning test method described in U.S. Pat. No. 4,474,678. These tests were run at approximately 75° F. and, like the low temperature detergency tests described in Example 3, gave similar results for both samples according to the invention and samples not according to the invention.

We claim as our invention:

1. A tertiary thiol ethoxylate composition having improved detergency properties and formulability, said composition comprising a mixture of ethoxylates of $C_9$ to $C_{16}$ tertiary thiols under conditions that
    (a) the average ethylene oxide adduct number of the $C_9$ to $C_{16}$ tertiary thiol ethoxylates is in the range from about 5 to 12 inclusive,
    (b) the concentration of $C_9$ to $C_{16}$ tertiary thiols in the compositions is less than about 0.08 percent by weight,
    (c) the concentration of the thiol ethoxylates having an ethylene oxide adduct number of one is less than about 0.1 percent by weight,
    (d) the concentration of the thiol ethoxylates having an adduct number of two is less than about 0.1 percent by weight, and
    (e) the concentration of the thiol ethoxylates having an ethylene oxide adduct number of three is less than about 1.6 percent by weight,
with each of such percentages calculated on the basis of the total weight of $C_9$ to $C_{16}$ tertiary thiol ethoxylates present in the composition.

2. The composition of claim 1, wherein
    (a) the concentration of C9 to C16 tertiary thiols is less than about 0.06 percent by weight,
    (b) the concentration of the thiol ethoxylates having an ethylene oxide adduct number of one is less than about 0.05 percent by weight, (c) the concentration of the thiol ethoxylates having an adduct number of two is less than about 0.06 percent by weight, and (d) the concentration of the thiol ethoxylates having an ethylene oxide adduct number of three is less than about 1.0 percent by weight.

3. The composition of claim 1, wherein the average ethylene oxide adduct number of the $C_9$ to $C_{16}$ tertiary thiol ethoxylates is in the range from about 6 to 9 inclusive.

4. The composition of claim 2, wherein the average ethylene oxide adduct number of the $C_9$ to $C_{16}$ tertiary thiol ethoxylates is in the range from about 6 to 10, inclusive.

5. The composition of claim 1, wherein
(a) the concentration of $C_9$ to $C_{16}$ tertiary thiols is less than about 0.03 percent by weight,
(b) the concentration of the thiol ethoxylates having an ethylene oxide adduct number of one is less than about 0.01 percent by weight,
(c) the concentration of the thiol ethoxylates having an adduct number of two is less than about 0.03 percent by weight, and
(d) the concentration of the thiol ethoxylates having an ethylene oxide adduct number of three is less than about 0.6 percent by weight.

6. The composition of claim 1, wherein the average ethylene oxide adduct number of the $C_9$ to $C_{16}$ tertiary thiol ethoxylates is in the range from about 6.5 to 7.5 inclusive.

7. The composition of claim 5, wherein the average ethylene oxide adduct number of the $C_9$ to $C_{16}$ tertiary thiol ethoxylates is in the range from about 6.5 to 7.5 inclusive.

8. A composition comprising a mixture of ethoxylates of $C_9$ to $C_{16}$ tertiary thiols,
(a) said mixture of ethoxylates having an average ethylene oxide adduct number in the range from about 5 to 12, inclusive, and
(b) said composition containing a total of less than 0.1 percent by weight of free $C_9$ to $C_{16}$ thiols and $C_9$ to $C_{16}$ tertiary thiol ethoxylates having ethylene oxide adduct numbers of 2 or less, said percentage calculated on the total weight of ethoxylates of $C_9$ to $C_{16}$ tertiary thiols.

9. The composition of claim 8, containing less than 0.03 percent by weight of free tertiary thiols.

10. The composition of claim 8, wherein the mixture of ethoxylates has an average ethylene oxide adduct number in the range from about 6 to.

11. The composition of claim 10, containing less than 0.03 percent by weight of free tertiary thiols.

12. The composition of claim 11, wherein the mixture of ethoxylates has an average ethylene oxide adduct number in the range from about 6.5 to 7.5.

13. A process for the preparation of a tertiary thiol ethoxylate composition having improved detergency properties and formulability which comprises the steps of (a) contacting and reacting, under ethoxylation conditions and in the presence of an ethoxylation catalyst, (i) one or more tertiary alkane thiols of the formula

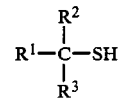

wherein $R^1$, $R^2$, and $R^3$ each individually represents an alkyl group having a carbon number in the range from about 1 to 10 and the sum of the carbon numbers of $R^1$, $R^2$, and $R^3$ is in the range from about 8 to 15, with (ii) sufficient ethylene oxide to produce a mixture of tertiary thiol ethoxylates of the formula

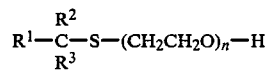

wherein n represents the ethylene oxide adduct number of the thiol ethoxylate molecule and n has an average value for the mixture which is in the range from about 5 to 12, said mixture also containing at least about 0.1 percent by weight of free thiol, and (b) heating the resulting tertiary thiol and tertiary thiol ethoxylate mixture to evaporate sufficient free thiol and lower ethylene oxide adducts to reduce the mixture's concentration of (i) free thiol to less than 0.08 percent by weight, (ii) thiol ethoxylates having an ethylene oxide adduct number of one to less than 0.1 percent by weight, (iii) thiol ethoxylates having an adduct number of two to less than 0.1 percent by weight, and (iv) thiol ethoxylates having an ethylene oxide adduct number of three to less than 1.6 percent by weight.

14. The process of claim 13, wherein the mixture is heated under vacuum in a thin film evaporator to evaporate free thiol and lower ethylene oxide adducts.

15. The process of claim 13, wherein the tertiary thiol and tertiary thiol ethoxylate mixture is heated to evaporate sufficient free thiol and lower ethylene oxide adducts to reduce the mixture's concentration of (i) free $C_9$ to $C_{16}$ thiols to less than 0.06 percent by weight, (ii) thiol ethoxylates having an ethylene oxide adduct number of one to less than 0.05 percent by weight, (iii) thiol ethoxylates having an adduct number of two to less than 0.06 percent by weight, and (iv) thiol ethoxylates having an ethylene oxide adduct number of three to less than 1.0 percent by weight.

16. The process of claim 15, wherein the mixture is heated under vacuum in a thin film evaporator to evaporate free thiol and lower ethylene oxide adducts.

17. The process of claim 15, wherein the tertiary thiol and tertiary thiol ethoxylate mixture is heated to evaporate sufficient free thiol and lower ethylene oxide adducts to reduce the mixture's concentration of (i) $C_9$ to $C_{16}$ free thiols to less than 0.03 percent by weight, (ii) thiol ethoxylates having an ethylene oxide adduct number of one to less than 0.01 percent by weight, (iii) thiol ethoxylates having an adduct number of two to less than 0.03 percent by weight, and (iv) thiol ethoxylates having an ethylene oxide adduct number of three to less than 0.6 percent by weight.

18. The process of claim 17, wherein the mixture is heated under vacuum in a thin film evaporator to evaporate free thiol and lower ethylene oxide adducts.

* * * * *